(12) United States Patent
Hall

(10) Patent No.: US 11,109,607 B2
(45) Date of Patent: Sep. 7, 2021

(54) OIL-BASED COMPOSITIONS FOR ENHANCING ORAL HEALTH AND GENERAL WELLNESS IN HUMANS

(71) Applicant: Gary Hall, Modesto, CA (US)

(72) Inventor: Gary Hall, Modesto, CA (US)

(*) Notice: Subject to any disclaimer, the term of this patent is extended or adjusted under 35 U.S.C. 154(b) by 168 days.

(21) Appl. No.: 14/547,046

(22) Filed: Nov. 18, 2014

(65) Prior Publication Data

US 2015/0139920 A1    May 21, 2015

Related U.S. Application Data

(60) Provisional application No. 61/905,731, filed on Nov. 18, 2013.

(51) Int. Cl.

| | | |
|---|---|---|
| *A23D 9/007* | (2006.01) | |
| *A61K 8/92* | (2006.01) | |
| *A61K 36/889* | (2006.01) | |
| *A61K 36/54* | (2006.01) | |
| *A61K 36/53* | (2006.01) | |
| *A61K 36/736* | (2006.01) | |
| *A61Q 11/00* | (2006.01) | |
| *A61K 31/20* | (2006.01) | |
| *A23D 9/00* | (2006.01) | |
| *A61Q 19/00* | (2006.01) | |
| *A61K 8/37* | (2006.01) | |
| *A23K 20/158* | (2016.01) | |
| *A23K 50/40* | (2016.01) | |
| *A23L 27/12* | (2016.01) | |
| *A23L 33/00* | (2016.01) | |
| *A23L 33/115* | (2016.01) | |

(52) U.S. Cl.
CPC ............... *A23D 9/007* (2013.01); *A23D 9/00* (2013.01); *A23K 20/158* (2016.05); *A23K 50/40* (2016.05); *A23L 27/12* (2016.08); *A23L 33/115* (2016.08); *A23L 33/30* (2016.08); *A61K 8/375* (2013.01); *A61K 8/922* (2013.01); *A61K 31/20* (2013.01); *A61K 36/53* (2013.01); *A61K 36/54* (2013.01); *A61K 36/736* (2013.01); *A61K 36/889* (2013.01); *A61Q 11/00* (2013.01); *A61Q 19/00* (2013.01)

(58) Field of Classification Search
CPC .......... A61K 8/922; A61K 9/007; A61K 9/00; A61K 36/889; A61K 36/54; A61K 36/736; A61K 31/20; A61K 2300/00; A61K 36/53; A61K 8/375; A61Q 11/00; A61Q 19/00; A23D 9/007; A23D 9/00; A23L 33/115; A23L 33/30; A23L 27/12; A23K 50/40; A23K 20/158
See application file for complete search history.

(56) References Cited

U.S. PATENT DOCUMENTS

| | | | | |
|---|---|---|---|---|
| 2,988,484 | A | * | 6/1961 | Barsky ................. C11C 3/10 424/554 |
| 4,067,997 | A | * | 1/1978 | Kabara ................ A01N 37/12 424/49 |
| 5,968,896 | A | | 10/1999 | Bell et al. |
| 9,687,429 | B2 | * | 6/2017 | Modak ................ A61K 8/365 |
| 2005/0207995 | A1 | * | 9/2005 | Gregory ............... A61Q 11/00 424/50 |
| 2007/0203237 | A1 | | 8/2007 | Brenna et al. |
| 2008/0031831 | A1 | * | 2/2008 | Laali ................... A61K 8/922 424/58 |
| 2008/0081840 | A1 | | 4/2008 | Myers et al. |
| 2011/0129552 | A1 | | 6/2011 | Saha et al. |
| 2012/0003163 | A1 | | 1/2012 | Mordas et al. |
| 2013/0123319 | A1 | * | 5/2013 | Bryan ................. A61K 9/0019 514/400 |
| 2013/0156708 | A1 | * | 6/2013 | Pesaro ................ A01N 31/08 424/59 |
| 2013/0224125 | A1 | * | 8/2013 | Kolazi ................. A61K 8/463 424/52 |
| 2013/0344120 | A1 | * | 12/2013 | Scott ................... A61P 31/04 424/401 |
| 2015/0139920 | A1 | | 5/2015 | Hall |

FOREIGN PATENT DOCUMENTS

| | | | |
|---|---|---|---|
| EP | 0797996 | | 10/1997 |
| JP | 358039614 | * | 3/1983 |
| WO | 2003020319 | | 3/2003 |
| WO | 2004012727 A1 | | 2/2004 |
| WO | 2006017627 A2 | | 2/2006 |
| WO | 2007070611 A2 | | 6/2007 |
| WO | 2014009923 | | 1/2014 |

OTHER PUBLICATIONS

International Search Report and Written Opinion for PCT/US2015/061124, dated Feb. 29, 2016.

* cited by examiner

*Primary Examiner* — Snigdha Maewall
(74) *Attorney, Agent, or Firm* — Magleby, Cataxinos & Greenwood, P.C.

(57) ABSTRACT

An oil-based composition comprises a glyceride of medium-chain fatty acids, at least one essential oil selected from the group consisting of cinnamon oil, oregano oil, avocado oil, coconut oil and apricot oil, and optionally cinnamon bark. The medium-chain fatty acid comprises about 6 to 12 carbon atoms. The oil-based composition may be used for oral hygiene applications, weight control applications, skin care applications, or treatment of *Staphylococcus aureus* infection.

6 Claims, No Drawings

OIL-BASED COMPOSITIONS FOR ENHANCING ORAL HEALTH AND GENERAL WELLNESS IN HUMANS

CROSS-REFERENCE TO RELATED APPLICATION

This application claims the benefit of U.S. Provisional Patent Application Ser. No. 61/905,731, filed Nov. 18, 2013, the disclosure of which is hereby incorporated herein in its entirety by this reference

TECHNICAL FIELD

Various aspects and embodiments relate generally to oil-based compositions for enhancing oral health and general wellness in animals, including humans, and to methods using such compositions.

BACKGROUND

Antiseptic mouthwashes have been widely used for the prevention and elimination of bad breath as well as for the reduction of oral microorganisms responsible for the development of dental plaque, tooth decay, and gum diseases. Antiseptic mouthwashes traditionally contain high levels of alcohol (i.e., ethanol), approximately 20% to 30% by volume based on total volume of the mouthwashes. Alcohol functions as a solvent for active ingredients and additives, such as astringents, fluorides, coloring agent and the like, in the mouthwashes. Furthermore, alcohol functions as a preservative for the mouthwashes during storage and use.

High levels of alcohol in mouthwashes could cause a feeling of gum burn and an unpleasant dry mouth sensation in some consumers. However, lowering the levels of alcohol in mouthwashes results in a reduced solubility of the active ingredients and other additives in the mouthwashes, and a decreased ability of the mouthwashes to kill the oral microorganisms responsible for bad breath, plaque and gum disease.

U.S. Patent Application, Publication No. 2012/0003163 discloses a mouthwash composition that is essentially free of C2-C4 monohydric alcohols. The mouthwash composition is a microemulsion consisting of oil-phase micelles in aqueous phase, wherein the total amount of oil phase does not exceed 1.35% weight based on total volume of the mouthwash composition. The mouthwash composition includes an oil phase of at least one antimicrobial essential oil, such as thymol, eucalyptol, menthol and methyl salicylate; a cosolvent system of polyol and either sugar alcohol or glycol; an alkylsulfate surfactant; and water.

Therefore, there is still a need for the mouthwashes containing a reduced amount of alcohol or no alcohol at all, and yet providing an enhanced ability to kill the oral microorganisms responsible for bad breath, plaque and gum disease.

Additionally, there has been increasing demand in general populations to enhance general wellness. That is to improve the complete physical and mental well-beings, and not merely to cure diseases or infirmity. Thus, there exists a need for new compositions capable of enhancing wellness.

Furthermore, there have been concerns about the microbial resistance to antibiotics, especially among staphylococcal strains, which present a major threat to public health. Since resistance by certain strains of *Staphylococcus* to multiple antibiotics like methicillin emerged in the late 1970's, many strategies to control antibiotic resistance have been proposed. Considering current therapeutic regimens, vancomycin usage has proven to be the most reliable to treat resistant staphylococcal infections. However, some staphylococcal strains have become resistant, at least to some extent, even to vancomycin. Multiple antibiotics of the same spectrum and low resistance potential have been used when single antibiotic substitutions are not effective.

Thus, there is a need for antimicrobial compositions that would provide low potential for developing the microbial resistance, especially among staphylococcal strains.

DETAILED DESCRIPTION

In one particular embodiment, an oil-based composition comprises a glyceride of medium-chain fatty acid, at least one essential oil selected from the group consisting of cinnamon oil, oregano oil, avocado oil, coconut oil and apricot oil, and optionally cinnamon bark.

As used herein, the term "glyceride of medium-chain fatty acids" means and includes a fatty acid ester of glycerol, wherein the fatty acid is a medium-chain fatty acid containing about 6 to 12 carbon atoms. The glyceride of medium-chain fatty acid may be monoglyceride, diglyceride, triglyceride, or mixtures thereof. The triglyceride of medium-chain fatty acid is also known in the healing arts as "medium-chain triglyceride" or "MCT oil." The triglyceride of medium-chain fatty acid may be derived from one or more types of medium-chain fatty acids. Non-limiting examples of medium-chain fatty acids may include caproic acid (C6 fatty acid), caprylic acid (C8 fatty acid), capric acid (C10 fatty acid), or lauric acid (C12 fatty acid).

In some embodiments, the glyceride of medium-chain fatty acids in the oil-based composition comprises a triglyceride of fatty acid containing six carbon atoms (i.e., caproic acid, C6 fatty acid). In some embodiments, the glyceride of medium-chain fatty acids in the oil-based composition comprises a triglyceride of fatty acid containing twelve carbon atoms (i.e., lauric acid, C12 fatty acid). In some embodiments, the glyceride of medium-chain fatty acids in the oil-based composition comprises a triglyceride of saturated fatty acids. In some embodiments, the glyceride of medium-chain fatty acids in the oil-based composition comprises monolaurin (i.e., monoglyceride of lauric acid).

In one further particular embodiment, the oil-based composition comprises an active ingredient consisting essentially of medium-chain triglyceride (MCT) oil, cinnamon bark, and at least one essential oil selected from cinnamon oil, oregano oil, avocado oil, coconut oil, and apricot oil In still further embodiment, the oil-based composition consists essentially of MCT oil, cinnamon bark, and at least one essential oil selected from the group consisting of cinnamon oil, oregano oil, avocado oil, coconut oil, and apricot oil.

In yet further embodiment, the oil-based composition consists essentially of MCT oil, cinnamon bark, cinnamon oil, oregano oil, avocado oil, coconut oil, and apricot oil.

The oil-based composition of present disclosure may be used for various applications. By way of non-limiting examples, the oil-based composition may be used for oral hygiene applications (e.g., mouthwashes), weight control applications (e.g., meal replacements or supplements), or skin care applications (e.g., lotions or skin healing ointments).

Without being bound to any theory, it is believed that the disclosed oil-based composition provides an enhanced antimicrobial performance because of its dual activities: desorbing the protein sheathed communities (i.e., biofilms) of microorganisms from the surfaces inside the mouth with its fatty acid functionalities; and killing the microorganisms with its antimicrobial essential oil ingredients. Thus, the disclosed oil-based composition not only kills the microorganisms in the mouth that cause bad breath, tooth decay and gum diseases, but also removes the biofilms of those microorganisms from the surfaces inside mouth to provide a long-lasting and more effective antimicrobial effect. The microorganisms in the mouth can be adsorbed into the body system and cause various health problems over time, such as weakening of gums and teeth in the mouth, deterioration of heart and other organs in the body, skin problems, skin disorders, and upset stomach.

In still further embodiment, the oil-based composition comprises monoglyceride of lauric acid (i.e., monolaurin), oregano oil, or a mixture thereof. Such oil-based compositions may provide antimicrobial activity with low potential for developing the microbial resistance, especially among staphylococcal strains.

Oral Hygiene Applications

The oil-based composition of present disclosure may provide antiviral, fungal and/or antimicrobial properties suitable for oral hygiene applications, such as mouthwashes.

In one particular embodiment, an oil-based mouthwash composition comprises a triglyceride of medium-chain fatty acids (MCT oil), cinnamon bark, and at least one essential oil selected from the group consisting of cinnamon oil, oregano oil, avocado oil, coconut oil, and apricot oil. The oil-based mouthwash composition is essentially alcohol-free.

When desired, the oil-based mouthwash composition may further include other oil-based active antimicrobial ingredients and/or additives.

In one further particular embodiment, an oil-based mouthwash composition comprises an active ingredient that consists essentially of MCT oil, cinnamon bark, and at least one essential oil selected from cinnamon oil, oregano oil, avocado oil, coconut oil, and apricot oil. The oil-based mouthwash composition is essentially free of alcohol and other chemical active ingredients. Thus, the oil-based mouthwash composition may be considered as organic, natural-based mouthwash.

In still further embodiments, the oil-based mouthwash composition consists essentially of MCT oil, cinnamon bark, and at least one essential oil selected from cinnamon oil, oregano oil, avocado oil, coconut oil, and apricot oil.

In some embodiments, the oil-based mouthwash composition consists essentially of MCT oil, cinnamon bark, cinnamon oil, oregano oil, avocado oil, coconut oil, and apricot oil.

In other embodiments, the oil-based mouthwash composition does not include thymol, eucalyptol, menthol, and methyl salicylate.

The oil-based composition of present disclosure may be used daily to enhance oral health. It may be beneficially used after brushing and flossing, since this is when bacteria, viral and/or fungal organisms enter the blood system. Additionally, the oil-based composition may be used while applying soft brushing to gums and teeth.

In one particular embodiment, a method of enhancing oral health comprises washing mouth with one tablespoon (about 14.8 grams) of the disclosed oil-based mouthwash composition for about 20 minutes twice daily.

Weight Control Applications

The oil-based composition of present disclosure may be used for weight control applications. By way of non-limiting examples, the oil-based composition may be used as meal replacements or food supplements.

As used herein, the term "weight control" means and include a predetermined action or set of actions which results in weight maintenance, weight loss, or weight gain less than would be anticipated.

In one particular embodiment, an oil-based meal replacement or supplement composition comprises a triglyceride of medium-chain fatty acids (MCT oil), cinnamon bark, and at least one essential oil selected from the group consisting of cinnamon oil, oregano oil, avocado oil, coconut oil, and apricot oil, wherein the medium-chain fatty acid comprises a saturated fatty acid including about 6 to 12 carbon atoms.

In one further particular embodiment, an oil-based meal replacement or supplement composition consists essentially of a triglyceride of medium-chain fatty acids (MCT oil), cinnamon bark, and at least one essential oil selected from the group consisting of cinnamon oil, oregano oil, avocado oil, coconut oil, and apricot oil. The medium-chain fatty acids of the triglyceride are saturated fatty acids.

In still further embodiments, the oil-based meal replacement or supplement composition consists essentially of MCT oil of saturated fatty acids, cinnamon bark, cinnamon oil, oregano oil, avocado oil, coconut oil, and apricot oil.

The disclosed oil-based composition may provide an energy boost quicker than typical energy boost compositions containing a triglyceride of long-chain fatty acids (LCT oil). This is because MCT oil in the disclosed composition can be converted to ketones to provide energy at a faster rate than LCT oil.

There have been continuingly increased health concerns on consumption of foods containing high amounts of saturated fats or oil (i.e., triglyceride of saturated fatty acids) or saturated fatty acids. For example, there have been extensive reports linking the consumption of saturated fat to an increased risk of cardiovascular diseases. Many health authorities, such as the American Heart Association, the American Dietetic Association, the United States Food and Drug Administration (USDA), the World Health Organization, the Dietitians of Canada, the British Dietetic Association, the British Heart Foundation, the World Heart Federation, the British National Health Service, and the European Food Safety Authority, have advised that saturated fat is a risk factor for cardiovascular diseases.

Even though there have been reports of using fatty acids and oils as meal replacements in weight control programs, these prior art meal replacements are based on unsaturated fatty acids or oil. For example, U.S. Patent Application, Publication No. 2008/0081840 describes the use of n-3 polyunsaturated fatty acids, including omega-3 fatty acids such as docosahexaenoic acid (DHA), α-linolenic acid (ALA) and eicosapentaenoic acid (EPA), as meal supplements in weight loss programs. The International Patent Application, Publication No. WO 2004/012727 discloses the use of nutrition supplements that contain long-chain polyunsaturated fatty acids (LC-PUFAs), especially n-3 long-chain polyunsaturated fatty acids such as DHA and arachidonic acid (AA), to control appetite and to help treating or preventing obesity and conditions of overweight. See also WO 2007/070611; WO 2006/017627; U.S. 2007/0203237.

Surprisingly and unexpectedly, it is now found clinically that not only the oil-based meal replacement or supplement composition of present disclosure may enhance weight loss, but also reduce the risk of cardiovascular diseases.

Furthermore, the oil-based composition of present disclosure may be used in the weight control program to suppress appetite.

In one particular embodiment, the disclosed oil-based meal replacement or supplement composition may be consumed about four tablespoons (about 60 grams) daily in the morning as a meal replacement and/or and an appetite suppressant.

In further embodiment, a method for controlling weight of a subject comprises orally administering about four tablespoons of the oil-based meal replacement or supplement composition to the subject every day in the morning.

In still further embodiment, a weight control plan comprises orally consuming about four tablespoons of the oil-based meal replacement or supplement composition in morning every day.

Skin Care Applications

The oil-based composition of present disclosure may be used for skin care applications, such as lotions or skin healing ointments for skin dryness, thermal burn, oil burn, and the like.

The oil-based skin care composition of present disclosure may be absorbed quickly and thoroughly through the skin. The composition may be hydrating and highly bio-accessible to skin to provide an enhanced and long-lasting hydration to the skin, without leaving the skin oily. Furthermore, the disclosed oil-based composition may help calming irritated skin after waxing.

The disclosed oil-based composition may be topically applied one tablespoon per application to body skin as needed.

In a particular embodiment, a method for treating skin of a subject comprises topically applying about one tablespoon of the oil-based composition of claim 1 to the subject as needed.

In a representative embodiment, the oil-based composition comprises:

about 300 mls MCT (may range from 250 mls to 350 mls);

about 100 mls organic coconut oil (may range from 75 mls to 125 mls);

about 100 mls avocado oil (may range from 75 mls to 150 mls);

about 0.75 mls cinnamon oil (may range from 0.5 mls to 1.0 mls);

about 1.25 mls oregano oil (may range from 1.0 ml to 1.5 mls);

about 0.50 mls apricot oil (may range from 0.25 mls to 0.75 mls); and about 2.5 inches organic cinnamon bark (may range from 2.0 to 3.0 inches).

The weight and size of the organic cinnamon bark may fluctuate slightly. While not being bound to any particular theory, the organic cinnamon bark is believed to act as a catalyst and carrier, which can cure the formula.

Animal Applications

The oil-based composition of present disclosure may be used on animals, such as companion animals (e.g., dogs, cats, etc.) for any of the indications described above, including, but not limited to: antiviral, antifungal, antimicrobial properties suitable for oral, skin, or internal dosing applications. Additional animal applications include use of the oil-based composition for wound cleaning/disinfecting, digestive tract treatment, and treatment of ear mites.

Treatment of *Staphylococcus aureus* Infection

*Staphylococcus aureus* infection may be effectively treated or prevented by daily administration of oregano oil, monolaurin, or a combination of both. Oregano oil is more effective in treating *Staphylococcus aureus* infection, compared to other essential oils, e.g., olive oil, pumpkin oil, fenugreek oil, myrtle oil, allspice oil, sage oil, lavender oil, bay leaf oil, cumin oil, cinnamon oil, and cassia oil. See Example 18, infra. Monolaurin also inhibits the growth of *Staphylococcus aureus* in vitro and in vivo to an extent similar to oregano oil. An unexpectedly enhanced efficacy against *Staphylococcus aureus* infection is achieved when oregano oil is used in combination with monolaurin. This suggests a likely synergistic effect when both oregano oil and monolaurin are used together in treating *Staphylococcus aureus* infection. Surprisingly, carvacrol does not provide the same efficacy against *Staphylococcus aureus* as the oregano oil at the same the phenol content. To achieve the same efficacy against *Staphylococcus aureus* as the oregano oil, carvacrol must be administered at twice the phenol content compared to the phenol content of one oregano oil dosage.

Thus, the daily oral administration of oregano oil and monolaurin, either alone or in combination, may prevent or treat *Staphylococcus aureus* infections. Additionally, such daily oral administration may be effective against antibiotic-resistant strains.

EXAMPLES

Example 1

Using the Disclosed Oil-Based Composition for Oral Care and Weight Control

A female subject was suffering from sore and bleeding gums. The subject indicated that upon washing her mouth with one tablespoon of the disclosed oil-based composition for about 20 minutes twice daily, she no longer suffered from sore and bleeding gums.

Additionally, the subject stated that by using the disclosed composition as meal replacement daily, she lost about 15 lbs.

Example 2

Using the Disclosed Oil-Based Composition for Oral Care

A male subject suffered from chronic tooth and gum problems caused by abscessed teeth. The subject indicated that upon using the disclosed composition for oral care, he no longer suffered from tooth and gum problems. His gums actually grew back to pre-abscess levels with the oral treatment of the disclosed composition.

Example 3

Using the Disclosed Oil-Based Composition for Oral Care and Skin Care

An 85 year old female subject that suffered from life-long chronic gum problems stated that she had to have teeth cleaning three times a year, instead of two times a year, as commonly needed for general populations.

The subject took the disclosed composition orally and applied it topically. After being treated with the disclosed composition for two weeks, the dental technician observed much improvement in oral health of the subject.

Additionally, the subject testified that she suffered from a painful corn on the top of her toe, which forced her to place a patch over the corn prior to wearing shoes. Upon topically applying the disclosed composition to the corn for about a month, the corn disappeared.

Example 4

Using the Disclosed Oil-Based Composition for Weight Control, Oral Care, and General Wellness A female subject stated that she lost a substantial amount of abdominal fat and a total weight of 7 lbs after taking the disclosed composition orally for three weeks. The subject also found that her chronic suffering from acid reflux had been cured or substantially subsided.

The subject further indicated that upon taking two tablespoons of the disclosed composition about one hour before going to bed, her insomnia disappeared and she no longer had to continually use the bathroom during the night, as had been happening for a significant number of weeks.

The subject also experienced an improved oral health for her teeth and gums by washing her mouth with the oil-based composition for 15 minutes, rinsing it out, and then brushing her teeth with the disclosed compound daily before going to bed.

Additionally, the subject stated that upon topically applying the disclosed oil-based compound onto severely sunburned areas of her face and arms, the peeling and flaking of her skin was prevented.

Example 5

Using the Disclosed Oil-Based Composition for Skin Care and Oral Care

A male subject tested the disclosed oil-based composition for a period of six weeks. The subject took one tablespoon of the disclosed oil-based composition orally twice a day (morning and evening), used the oil-based composition as mouthwash every morning, and applied the oil-based composition topically on his forehead, face, arms, and hands. The subject testified that at the end of six-week period, he experienced fewer problems with bad breath. Additionally, the oil-based composition was very effective at alleviating dry skin on his forehead, arms, and hands.

Example 6

Using the Disclosed Oil-Based Composition for Oral Care

A female subject had an abscessed tooth and experienced intense pain, which also led to swelling on her chin. The subject took a tablespoonful of the disclosed composition and held it in her mouth for four minutes before splitting it out and rinsing her mouth with water. The subject stated that with the treatment, the areas in her mouth around the abscessed tooth became numb and the pain subsided.

Example 7

Using the Disclosed Oil-Based Composition as Healing Ointment for Oil Burn

A female subject that suffered from a cooking oil burn was treated with the disclosed oil-based composition. After the back sides of her fingers were burned by hot cooking oil from a deep fryer pot, the female subject immediately applied cool water to the burns. The next morning, the burned areas became blistered, so the subject applied the disclosed oil-based composition as a healing ointment to the burned areas. The subject stated that her burned skin started to scab up by evening of the day that she first applied the disclosed composition. The subject continued to apply the oil-based composition twice daily (morning and night) and testified that by the third day, the burned skin sloughed off, revealing healthy new skin.

Example 8

Using the Disclosed Oil-Based Composition as Meal Supplements and as Skin Care Ointments A female subject used the disclosed oil-based composition as topical skin care for her face and body. After using the disclosed composition for about one month, the subject noticed that her skin looked much more hydrated and healthy. Further, the subject applied the disclosed composition topically to her skin after waxing, and found that the disclosed compound helped to sooth and calm the sensitive and/or irritated post-waxed skin.

Additionally, the subject added about one tablespoon of the disclosed composition to her morning smoothie for about one month. She testified that she lost about 6 lbs after one month of using the disclosed compound as a meal replacement in her daily morning smoothie.

The subject also applied the disclosed composition topically in her nose. She testified that the disclosed compound calmed her seasonal allergies, kept her sinuses hydrated and prevented her from catching airborne diseases when traveling on the plane.

Example 9

Using the Disclosed Oil-Based Composition as Skin Healing Ointment for Shingles

A female subject that suffered from shingles was treated with the disclosed oil-based composition. The subject experienced painful rashes and blisters on his left ribcages that spread from left ribcage up to his left breast within a day, resulting in increasing pain and itching. After three days, the subject went to see a physician and was diagnosed as suffering from shingles. The subject was prescribed valacyclovir (VALTREX®), which is an anti-viral medication commonly used for treatment of shingles. However, the subject hesitated and refused to use valacyclovir medication. Instead, he took one tablespoonful of the disclosed composition daily and also applied the disclosed composition topically on the shingles daily. The subject stated that after only two days of the oral and topical treatments, the shingle blisters were smaller, the lesions were totally healed, and the pain had subsided. The subject further testified that his symptoms from shingles completely ceased after oral and topical treatments with the disclosed composition, without having to use any medications typical applied for shingles treatment.

Example 10

Using the Disclosed Oil-Based Composition as Skin Healing Ointment

A 65-year old male subject experienced dry scaly skin problems on his forearms and elbows, and reddish skin areas on his face. The subject testified that his skin problems have significantly subsided upon applying the disclosed composition topically to the affected skin areas.

Example 11

Using the Disclosed Oil-Based Composition as Wellness and Weight Control Supplements A female subject aged 58 years old who chronically suffered from acid reflux, insomnia, and forgetfulness was treated with the disclosed oil-based composition. The subject testified that after four days of the treatment (4 tablespoons every morning), she no longer suffered from acid reflux. Her insomnia was cured, and she could sleep restfully at night and feel refreshed in the morning. Furthermore, she felt less anxious and experienced less forgetfulness.

The subject also experienced bleeding and painful gums whenever she flossed her teeth, especially her front teeth. The subject testified that with the oral hygiene treatment using the disclosed composition, she no longer noticed any painful or bleeding gums when she flossed her teeth.

Furthermore, the subject testified that the treatment with disclosed composition had eased, if not cured, bloating, stomachaches, and sensational burn feeling in her stomach. The subject also testified that within two weeks of the treatments, she experienced a significant abdominal fat loss and a total weight loss of 5 lbs.

Example 12

Using the Disclosed Oil-Based Composition for Weight Control and General Wellness A female subject stated that after taking the disclosed composition orally for about a month and a half (4 tablespoons every day), she felt much more energetic and no longer suffered from the feeling of low energy that she experienced daily, especially in the mid afternoon. The disclosed composition helped suppressing her appetite. Before the treatment, she typically woke up 3-4 times a night and could not get a restful sleep. The subject testified that after the treatment, she experienced much improved and restful sleep.

Example 13

Using the Disclosed Oil-Based Composition for Weight Control and Oral Care

A female subject who had tried to lose weight without much success stated that by using the disclosed composition (3-4 tablespoons every morning), she was able to lose a total of 15 pounds within one month of the treatment, without other alterations to her diet or exercise regimen. She experienced less craving for sugar, and yet felt more energetic. The subject also noticed less dryness in her mouth, and her teeth and gums felt healthier.

Example 14

Using the Disclosed Oil-Based Composition as Food Supplements for General Wellness A male subject that suffered from gout stated that after using the disclosed oil-based composition as a food supplement, he noticed a significant diminishing of gout symptoms.

Example 15

Using the Disclosed Oil-Based Composition for Weight Control and Reduction of Cholesterol, LDL, and Triglycerides A male subject started taking 4 tablespoons of the oil-based formula per day for weight control. Lab tests were run before the initiation of treatment and tests were run again approximately 90 days post treatment. The lab results showed reduction in total cholesterol (from 238 to 179), reduction in LDL (from 160 to 118), and triglycerides (from 166 to 9). The subject lost approximately 20 lbs during this time frame. I have been using the product as a meal replacement, taking 2-4 tablespoons in the am. The subject states that his food cravings and appetite were suppressed.

Example 16

Using the Disclosed Oil-Based Composition for Treatment of a Stye

A female subject started developing a stye on her left eye. She applied a warm compress, but the pain did not subside. She coated the stye with a layer of the oil-based composition and the pain and swelling of the stye was completely eliminated in 20 minutes.

Example 17

Using the Disclosed Oil-Based Composition for Treatment of Canker Sores

A female subject started developing a canker sore inside her mouth. She contacted the canker sore with the oil-based composition for approximately 15 minutes and the pain and appearance of the canker sore disappeared after a few hours.

Example 18

Using the Disclosed Oil-Based Composition for Treatment of *Staphylococcus aureus*

Animals and Treatment

Female BALB/c mice (about 15 grams to 20 grams in weight) were obtained from Taconic Farms (Germantown, N.Y.). The mice were maintained in a controlled environment at about 24° C. with a 12-hour light and 12-hour dark cycle and were acclimatized in the animal facility for about 3-5 days before testing. The mice were housed in groups of five, fed commercial rodent pellets, and given water ad libitum throughout the experiments. The Animal Welfare Board at Georgetown University Medical Center approved the protocol for the entire investigation.

Plant Oils and Chemicals

Oregano oil (P73 Oreganol™ product, which is a blend of edible species of wild oregano grown on natural, mineral-rich soil from the Mediterranean), olive oil, and other essential oils (pumpkin oil, fenugreek oil, myrtle oil, allspice oil, sage oil, lavender oil, bay leaf oil, cumin oil, cinnamon oil, and cassia oil) were available from North American Herb and Spices, Inc., Waukegan, Ill., USA. Monolaurin (glycerol monolaurate) was obtained from the Center for Research on Lauric Oils, Bethesda, Md., USA (www.lauric.org). Sabouraud's glucose (S.g.) broth and agar media were obtained from Difco Laboratories (Detroit, Mich., USA). Carvacrol, antibiotics, and all other chemicals used in the study were obtained from Sigma Chemical Co. (St. Louis, Mo., USA) and were of analytical grade or the highest commercial grade available.

Organisms

Standard strains of *Staphylococcus* (ATCC #14154 and ATCC #14775) were obtained from ATCC, Fairfax, Va., USA, and were grown and maintained on S.g. agar slants.

Susceptibility Testing

A micro-broth dilution technique was used to determine the susceptibility of the strains of *Staphylococcus aureus*. Susceptibility was expressed as minimum inhibitory (MIC) and/or minimum bactericidal (MBC) concentration.

Various essential oils, carvacrol, and monolaurin were tested alone or in combination for the treatment of *Staphylococcus aureus* infection. Twelve essential oils were tested in the study: oregano oil, olive oil (the diluent), pumpkin oil, fenugreek oil, myrtle oil, allspice oil, sage oil, lavender oil, bay leaf oil, cumin oil, cinnamon oil, and cassia oil.

The stock solutions of oregano oil, other essential oils, olive oil, and carvacrol were dissolved in 50% ethanol-Tween 80 solvents. Antibiotics were dissolved in 50% ethanol and used as positive controls. Solvent controls (addition of carrier without essential oil and monolaurin) were also included for reference in addition to regular controls.

The Sabouraud's glucose (S.g.) broth containing varying amounts (logarithmic, serially and 2-fold diluted) of oregano oil, other essential oils, carvacrol, monolaurin and various controls were inoculated with actively dividing *Staphylococcus aureus* cells. The cultures were incubated for about 24 hours and about 48 hours at a temperature of about 30° C. on a metabolic rotary shaker (220 rev/min), and the growth was monitored both visually and colorimetrically (at a wavelength of about 40 nm). The minimum inhibitory concentration (MIC) was defined as the lowest concentration required to arrest the growth of the bacteria at the end of 24 hour of incubation. Minimum bactericidal concentration (MBC) was determined by sub-culturing a 0.01 ml aliquot of the medium drawn from the culture tubes after 48 hours on S.g. agar plates and incubated further for bacterial growth. The plates were scored for growth of the bacteria colonies. The lowest concentration of the antimicrobial agent causing negative growth (fewer than three colonies) was considered as MBC. In every case, the MIC and MBC were virtually the same.

In Vivo Study

In two separate experiments, groups of mice (6 and 8 respectively) infected with *Staphylococcus aureus* ($5 \times LD_{50}$) were gavaged daily with oregano oil, carvacrol, monolaurin or combined oregano oil-monolaurin in 0.2 ml of olive oil for 30 days. The amount of bacterial agents administered was calculated based on the body weight of the mice. Control mice received daily gavages of either olive oil alone (negative control) or olive oil orally plus vancomycin (400 mcg) i.p. (positive control).

In the first in vivo experiment, the daily dose of oregano oil was either 2.0 µl (1.6 mg) or 4.0 µl (3.2 mg). The mice gavaged with carvacrol received doses comparable to the phenol content in the two doses of oregano oil. In the second in vivo study, the daily dose of oregano oil was the same as the higher dose used before, i.e., 4.0 µl (3.2 mg). Monolaurin was given at the same dose; and when both agents were combined, the same individual doses were used, i.e., 3.2 mg of each. Both experiments were terminated at the end of 30 days. The body weight, the disease status, and the overall health of the mice during the experiments were recorded. The pathological status of the mice was determined by visual examination of the internal organs after their death or sacrifice at the completion of the experiment. Culturing aliquots of kidney homogenates on S.g. agar plates were tested for the renal burden of *Staphylococcus aureus*.

Comparative Study of Various Antibiotics and Essential Oils Against *Staphylococcus aureus* (ATCC#14154) Infection A micro dilution study on *Staphylococcus aureus* (ATCC#14154) grown in broth over 48 hours was performed to determine the comparative effects of various antibiotics and essential oils against *Staphylococcus aureus* infection at the selected concentrations.

The antibiotics used in the study were penicillin, streptomycin, and vancomycin. Penicillin essentially showed no effect against *Staphylococcus aureus* (ATCC#14154). Streptomycin did not completely kill the bacteria. Vancomycin completely destroyed the bacteria. The solvent control (i.e., addition of the carrier alone to the plates) did not alter growth.

Of the twelve essential oils examined, olive oil (the diluent), pumpkin oil, fenugreek oil, and myrtle oil showed virtually no effect against *Staphylococcus aureus* at any concentration. Allspice oil, sage oil, lavender oil, and bay leaf oil were bactericidal against *Staphylococcus aureus* only at higher concentrations. Cumin oil had an intermediate effect, while cinnamon oil, cassia oil, and oregano oil were quite effective against *Staphylococcus aureus* at lower concentrations.

The efficacy of carvacrol against *Staphylococcus aureus* was tested at a concentration equivalent to the total phenol content in a similar volume of oregano oil (63% v/v). While oregano oil showed a complete bactericidal activity at a concentration of 0.25 mg, the carvacrol was effective against *Staphylococcus aureus* only at the concentration comparable to the 0.5 mg dose of oregano oil.

Comparative Study of Various Antibiotics and Essential Oils Against *Staphylococcus aureus* (ATCC#14775) Infection The micro dilution study was performed with another strain of *Staphylococcus aureus* (ATCC#14775). Although the results from the two strains (ATCC#14775 and ATCC#14154) were generally similar, there were some minor differences. Myrtle oil appeared relatively more effective against the ATCC #14775 strain. Cumin oil seemed to work as well as cassia oil against the ATCC#14775 strain. Oregano oil provided efficacy against the ATCC#14775 strain infections at the concentration as low as 0.25 mg oregano oil. Carvacrol provided efficacy against the ATCC#14775 strain infections at a phenol content equivalent to that in 0.5 mg oregano oil.

In Vitro Study

The in vitro experiment on *Staphylococcus aureus* (ATCC#14775) was performed to investigate the efficacy of using monolaurin alone, using monolaurin in combination with oregano oil, or using oregano oil alone. A few *Staphylococcus aureus* (ATCC#14775) colonies grew after two days of incubation in 0.125 mg of oregano oil or 0.125 mg of monolaurin. However, a combination of 0.125 mg oregano oil and 0.125 mg monolaurin prevented any growth of *Staphylococcus aureus* (ATCC#14775).

Furthermore, the in vivo therapeutic effects of the natural edible oregano oil and one of its major constituents, carvacrol, were examined in a murine systemic bacteremia model. Preliminary studies showed that *Staphylococcus aureus* (ATCC#14154) did not cause mortality or death in mice; whereas, *Staphylococcus aureus* (ATCC#14775) caused mortality rapidly. Groups of six mice infected with *Staphy-* lococcus aureus (ATCC#14775) (5×LD$_{50}$) were gavaged with varying amounts of oregano oil (2.0 µl 1.6 mg; and 4.0 µl 3.2 mg) or injected i.p. with vancomycin (400 µg) daily for 30 days. A dose dependent survival was observed in the mice receiving oregano oil. Fifty percent of the mice (3/6) receiving oregano oil (3.2 mg) survived over the thirty days, while only one of six receiving 1.6 mg oregano oil survived for 30 days. Also, 50% of those receiving vancomycin (400 µg) survived for 30 days, while all in the control group died within a three-day period. Although prolonged survival was noted in the mice gavaged with carvacrol, none of the twelve mice at the two doses equivalent to the total phenol content in 1.6 mg and 3.2 mg of oregano oil survived beyond 21 days. In all 30-days survivors, no internal abscesses were noted at post mortem, and renal cultures showed no bacterial growth. In contrast, numerous abscesses were noted and renal cultures were positive in all dying mice.

In a separate in vivo study, the effects of using monolaurin, either alone and in combination with oregano oil, were investigated and compared to the effects of oregano oil alone. Groups of eight mice were infected with five times the LD$_{50}$ (5×LD$_{50}$) of *Staphylococcus aureus* (A TIC #14775). Fifty percent of the mice (4/8) injected daily with vancomycin (400 µg i.p.) survived for the thirty days of study in contrast to the control group where all eight mice died within a week's time. In the three test groups, 3/8 survived for 30 days in the oregano oil group (3.2 mg), 4/8 survived in the monolaurin group (3.2 mg), and 5/8 survived in the group receiving the combination of oregano oil (3.2 mg) and monolaurin (3.2 mg). No abscesses were seen on inspection, and no bacterial growth was found in the kidney tissue of the 30-day survivors.

Efficacies of Oregano oil, Carvacrol, Certain Other Essential Oils, and Monolaurin Against *Staphylococcus aureus* (ATCC #14775) Infection Oregano oil, a constituent carvacrol, certain other essential oils, and monolaurin killed *Staphylococcus aureus* effectively in vitro. Furthermore, oregano oil and monolaurin showed protective effect against *Staphylococcus aureus* infection in vivo. In the fourteen mice used as control, *Staphylococcus aureus* (ATCC #14775) killed all the mice within 7 days. In contrast, about 37.5% to 50% of the mice survived for thirty day after receiving daily gavages of vancomycin (7/14), oregano oil (6/14), and monolaurin (4/8). The survival with combined oregano oil and monolaurin was slightly better, e.g., 62.5% survival rate (5/8). No abscesses were found at post mortem. Additionally, *Staphy-lococcus aureus* could not be grown out of the kidneys of the 30-day survivor, thus suggesting a cure.

Carvacrol gavaged in a dose calculated to be equivalent to the phenol content in the gavaged oregano oil delayed death but could not cure the mice. In the first in vivo study where carvacrol was examined, all untreated mice died within three days; whereas, all mice receiving carvacrol lived beyond three days, but died by 21 days. *Staphylococcus aureus* was grown out of their kidneys after death of these mice. Thus, carvacrol alone could not duplicate, to the same extent, the beneficial effects of oregano oil.

While this invention has been described in certain embodiments, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

The invention claimed is:

1. An oil-based mouthwash composition comprising:
   a glyceride of medium-chain fatty acids, wherein the medium-chain fatty acid comprises about 6 to 12 carbon atoms;
   cinnamon bark; and
   at least one essential oil selected from the group consisting of cinnamon oil, oregano oil, avocado oil, coconut oil, and apricot oil, and
   wherein the mouthwash composition is essentially free of alcohol and water and reduces biofilm in the mouth.

2. The mouthwash composition of claim 1, wherein the active oil-based ingredient does not include thymol, eucalyptol, menthol, and methyl salicylate.

3. The mouthwash composition of claim 1, wherein the glyceride of medium-chain fatty acids is a triglyceride.

4. The mouthwash composition of claim 1, wherein the glyceride of medium-chain fatty acids comprises a monoglyceride, a diglyceride, a triglyceride, or a mixture thereof.

5. The mouthwash composition of claim 1, wherein the medium-chain fatty acid is a saturated fatty acid.

6. The mouthwash composition of claim 1, wherein the glyceride of medium-chain fatty acids comprises a monoglyceride of lauric acid, and wherein the at least one essential oil is oregano oil.

* * * * *